United States Patent
Silverman et al.

(10) Patent No.: US 9,970,032 B2
(45) Date of Patent: May 15, 2018

(54) BIOREFINERY SYSTEM, METHODS AND COMPOSITIONS THEREOF

(71) Applicant: Calysta, Inc., Menlo Park, CA (US)

(72) Inventors: Joshua A. Silverman, Los Altos Hills, CA (US); Sol M. Resnick, Encinitas, CA (US); Michael Mendez, San Diego, CA (US)

(73) Assignee: Calysta, Inc., Menlo Park, CA (US)

( * ) Notice: Subject to any disclaimer, the term of this patent is extended or adjusted under 35 U.S.C. 154(b) by 0 days. days.

(21) Appl. No.: 14/886,983

(22) Filed: Oct. 19, 2015

(65) Prior Publication Data

US 2016/0040198 A1 Feb. 11, 2016

Related U.S. Application Data

(62) Division of application No. 13/940,861, filed on Jul. 12, 2013.

(Continued)

(51) Int. Cl.
*C10L 1/02* (2006.01)
*C10L 1/04* (2006.01)
(Continued)

(52) U.S. Cl.
CPC .............. *C12P 7/6409* (2013.01); *C10G 3/00* (2013.01); *C10G 3/50* (2013.01); *C10G 47/00* (2013.01);
(Continued)

(58) Field of Classification Search
CPC .... C10G 2300/1014; C10G 3/00; C10G 3/50; C10G 47/00; C10L 1/02; C10L 1/04; C10L 2200/0469; C10L 2270/02; C10L 2270/04; C10L 2290/26; C12N 15/74; C12N 1/16; C12N 1/20; C12N 9/1029; C12N 9/16;
(Continued)

(56) References Cited

U.S. PATENT DOCUMENTS 4,269,940 A 5/1981 Patel et al.
6,492,135 B1 12/2002 Larsen
(Continued)

FOREIGN PATENT DOCUMENTS

EP 0 296 484 A2 12/1988
EP 1 265 982 B1 9/2004
(Continued)

OTHER PUBLICATIONS

Keeling et al., "Monthly Atmospheric $^{13}C/^{12}C$ Isotopic Ratios for 11 SIO Stations," Trends: A Compendium of Data on Global Change. Carbon Dioxide Information Analysis Center, Oak Ridge National Laboratory, U.S. Department of Energy, Oak Ridge, Tenn., U.S.A. (3 pages) (Feb. 16, 2010).

(Continued)

*Primary Examiner* — Latosha Hines
(74) *Attorney, Agent, or Firm* — Seed IP Law Group LLP

(57) ABSTRACT

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

22 Claims, 1 Drawing Sheet

Related U.S. Application Data

(60) Provisional application No. 61/671,542, filed on Jul. 13, 2012.

(51) Int. Cl.

| | | |
|---|---|---|
| *C12P 7/64* | (2006.01) | |
| *C12N 15/74* | (2006.01) | |
| *C12P 5/00* | (2006.01) | |
| *C10G 3/00* | (2006.01) | |
| *C12N 9/16* | (2006.01) | |
| *C12N 9/00* | (2006.01) | |
| *C12N 1/16* | (2006.01) | |
| *C12N 1/20* | (2006.01) | |
| *C12N 9/10* | (2006.01) | |
| *C10G 47/00* | (2006.01) | |
| *C12N 15/52* | (2006.01) | |
| *C12R 1/01* | (2006.01) | |

(52) U.S. Cl.
CPC .................................. *C10L 1/02* (2013.01); *C10L 1/04* (2013.01); *C12N 1/16* (2013.01); *C12N 1/20* (2013.01); *C12N 9/1029* (2013.01); *C12N 9/16* (2013.01); *C12N 9/93* (2013.01); *C12N 15/52* (2013.01); *C12N 15/74* (2013.01); *C12P 5/00* (2013.01); *C12P 7/649* (2013.01); *C12P 7/6463* (2013.01); *C12R 1/01* (2013.01); *C12Y 203/01039* (2013.01); *C12Y 301/02* (2013.01); *C12Y 602/01003* (2013.01); *C12Y 604/01002* (2013.01); *C10G 2300/1014* (2013.01); *C10L 2200/0469* (2013.01); *C10L 2270/02* (2013.01); *C10L 2270/04* (2013.01); *C10L 2290/26* (2013.01); *Y02E 50/13* (2013.01); *Y02E 50/343* (2013.01); *Y02P 20/52* (2015.11); *Y02P 30/20* (2015.11)

(58) Field of Classification Search
CPC ... C12N 9/93; C12N 15/52; C12P 5/00; C12P 7/6409; C12P 7/6463; C12P 7/649; C12Y 203/01039; C12Y 301/02; C12Y 602/01003; C12Y 604/01002; Y02E 50/13; Y02E 50/343; Y02P 20/52; Y02P 30/20; C12R 1/01
USPC .................................................. 585/606, 639
See application file for complete search history.

(56) References Cited

U.S. PATENT DOCUMENTS

| | | | |
|---|---|---|---|
| 6,689,601 B2 | 2/2004 | Koffas et al. | |
| 6,818,424 B2 | 11/2004 | DiCosimo et al. | |
| 7,026,464 B2 | 4/2006 | Dicosimo et al. | |
| 7,098,005 B2 | 8/2006 | Dicosimo et al. | |
| 7,579,163 B2 | 8/2009 | Eriksen et al. | |
| 7,799,550 B2 | 9/2010 | Moen et al. | |
| 8,062,392 B2 | 11/2011 | Bryan et al. | |
| 8,093,306 B2 | 1/2012 | Blevins et al. | |
| 8,129,154 B2 | 3/2012 | Burk et al. | |
| 8,129,155 B2 | 3/2012 | Trawick et al. | |
| 8,153,850 B2 | 4/2012 | Hall et al. | |
| 8,168,686 B2 | 5/2012 | Blevins et al. | |
| 8,173,044 B1 | 5/2012 | Cheiky et al. | |
| 8,177,870 B2 | 5/2012 | Herrema et al. | |
| 8,592,198 B2 | 11/2013 | Moen et al. | |
| 2002/0137190 A1* | 9/2002 | Koffas .................. C12N 1/20 435/252.3 | |
| 2003/0003528 A1 | 1/2003 | Brzostowicz et al. | |
| 2005/0054030 A1* | 3/2005 | Schnoor .................. A62D 3/02 435/41 | |
| 2005/0163802 A1 | 7/2005 | Jorgensen et al. | |
| 2006/0057726 A1* | 3/2006 | Sharpe .................. C12N 9/00 435/471 |
| 2008/0026005 A1 | 1/2008 | Miguez et al. | |
| 2008/0057554 A1 | 3/2008 | Huhnke et al. | |
| 2009/0263877 A1 | 10/2009 | Eriksen et al. | |
| 2010/0068772 A1* | 3/2010 | Downey .................. C12N 1/06 435/134 |
| 2010/0221813 A1 | 9/2010 | Miguez et al. | |
| 2010/0248344 A1 | 9/2010 | Schroder et al. | |
| 2010/0251601 A1 | 10/2010 | Hu et al. | |
| 2010/0297749 A1* | 11/2010 | Aravanis .................. C12M 21/02 435/289.1 |
| 2011/0162259 A1 | 7/2011 | Gaertner | |
| 2011/0165639 A1* | 7/2011 | Ascon .................. C12M 21/12 435/134 |
| 2011/0236919 A1 | 9/2011 | Zahn et al. | |
| 2011/0306100 A1 | 12/2011 | De Crecy | |
| 2012/0003705 A1 | 1/2012 | Jin et al. | |
| 2012/0070870 A1 | 3/2012 | Way et al. | |
| 2012/0116138 A1* | 5/2012 | Goodall .................. C10G 45/08 585/357 |
| 2012/0142983 A1 | 6/2012 | Vermeiren et al. | |
| 2012/0190088 A1* | 7/2012 | Lee .................. C12N 9/20 435/134 |
| 2013/0189763 A1 | 7/2013 | Dalla-Betta et al. | |
| 2014/0013658 A1 | 1/2014 | Silverman et al. | |
| 2015/0218508 A1 | 8/2015 | Silverman et al. | |

FOREIGN PATENT DOCUMENTS

| | | |
|---|---|---|
| EP | 1 497 409 B1 | 5/2006 |
| EP | 1 183 326 B1 | 3/2007 |
| EP | 1 478 376 B1 | 9/2010 |
| EP | 1 419 234 B1 | 3/2011 |
| EP | 2 455 484 A2 | 5/2012 |
| EP | 2 427 200 B1 | 4/2014 |
| WO | 01/60974 A2 | 8/2001 |
| WO | 02/18617 A2 | 3/2002 |
| WO | 03/016460 A1 | 2/2003 |
| WO | 03/068003 A1 | 8/2003 |
| WO | 03/072133 A2 | 9/2003 |
| WO | 03/089625 A2 | 10/2003 |
| WO | 2007/136762 A2 | 11/2007 |
| WO | 2008/119082 A2 | 10/2008 |
| WO | 2009/009391 A2 | 1/2009 |
| WO | 2009/140695 A1 | 11/2009 |
| WO | 2009/151342 A1 | 12/2009 |
| WO | WO 2009151342 A1 * | 12/2009 ............... C12N 1/20 |
| WO | 2010/062480 A2 | 6/2010 |
| WO | 2010/128312 A2 | 10/2010 |
| WO | WO 2010124030 A1 * | 10/2010 ............. C10G 45/08 |
| WO | WO 2011008058 A2 * | 1/2011 ............... C12N 9/20 |
| WO | 2011/038132 A1 | 3/2011 |
| WO | 2011/044279 A2 | 4/2011 |
| WO | 2012/045022 A2 | 4/2012 |
| WO | 2012/08071 A2 | 6/2012 |
| WO | 2014/012055 A1 | 1/2014 |

OTHER PUBLICATIONS

Kendall et al., "Resources on Isotopes—Periodic Table—Carbon," Isotope Tracers Project, Menlo Park, Calif. (4 pages) http://wwwrcamnl.wr.usgs.gov/isoig/period/c_iig (1995).

Park et al., "Metabolic Fractionation of $C^{13}$ & $C^{12}$ in Plants," *Plant Physiology* 36(2):133-138 (Mar. 1961).

Chen, "A microbial polyhydroxyalkanoates (PHA) based bio- and materials industry," *Chem. Soc. Rev.* 38:2434-2446, 2009.

Fang et al., "Characterization of methanotrophic bacteria on the basis of intact phospholipid profiles," *FEMS Microbiology Letters* 189:67-72, 2000.

Folch et al., "A Simple Method for the Isolation and Purification of Total Lipides From Animal Tissues," *J. Biol. Chem.* 226(1):497-509, May 1957.

Hanson et al., "Methanotrophic Bacteria," *Microbiological Reviews* 60(2):439-471, Jun. 1996.

(56) References Cited

OTHER PUBLICATIONS

Helm et al., "Characterizing a stable methane-utilizing mixed culture used in the synthesis of a high-quality biopolymer in an open system," *Journal of Applied Microbiology* 101:387-395, 2006.

Henstra et al., "Microbiology of synthesis gas fermentation for biofuel production," *Current Opinion in Biotechnology* 18:200-206 (2007).

Höfer et al., "Production of functionalized polyhydroxyalkanoates by genetically modified *Methylobacterium extorquens* strains," *Microbial Cell Factories* 9:70, 2010, 13 pages.

Jahnke, "The effects of growth temperature on the methyl sterol and phospholipid fatty acid composition of *Methylococcus capsulatus* (Bath)," *FEMS Microbiology Letters* 93:209-212 (1992).

Kaluzhnaya et al., "Taxonomic Characterization of New Alkaliphilic and Alkalitolerant Methanotrophs from Soda Lakes of the Southeastern Transbaikal Region and description of *Methylomicrobium buryatense* sp.nov.," System. Appl. Microbiol. 24:166-176 (2001).

Kim et al., "Creating auxotrophic mutants in *Methylophilus methylotrophus* AS1 by combining electroporation and chemical mutagenesis," *Appl. Microbiol. Biotechnol.* 48:105-108, 1997.

Kosa et al., "Lipids from heterotrophic microbes: advances in metabolism research," *Trends in Biotechnology* 29(2):53-61 (Feb. 2011).

Lee et al., "Heterologous Co-expression of *accA*, *fabD*, and Thioesterase Genes for Improving Long-Chain Fatty Acid Production in *Pseudomonas aeruginosa* and *Escherichia coli*," *Appl Biochem Biotechnol* 167:24-38 (2012).

Madison et al., "Metabolic Engineering of Poly(3-Hydroxyalkanoates): From DNA to Plastic," *Microbiology and Molecular Biology Reviews* 63(1):21-53, Mar. 1999.

Marx et al., "Development of improved versatile broad-host-range vectors for use in methylotrophs and other Gram-negative bacteria," *Microbiology* 147:2065-2075, 2001.

McDonald et al., "Molecular Ecology Techniques for the Study of Aerobic Methanotrophs," *Applied and Environmental Microbiology* 74(5): 1305- 1315, Mar. 2008.

Ramsay et al., "Production of Poly-(β-Hydroxybutyric-Co-β-Hydroxyvaleric) Acids," *Applied and Environmental Microbiology* 56(7):2093-2098, Jul. 1990.

Schrader et al., "Methanol-based industrial biotechnology: current status and future perspectives of methylotrophic bacteria," *Trends in Biotechnology* 27(2):107-115 (Feb. 1, 2009).

Stolyar et al., "Role of multiple gene copies in particulate methane monooxygenase activity in the methane-oxidizing bacterium *Methylococcus capsulatus* Bath," *Microbiology* 145:1235-1244, 1999.

Summons et al., "Carbon isotopic fractionation in lipids from methanotrophic bacteria: Relevance for interpretation of the geochemical record of biomarkers," *Geochimica et Cosmochimica Acta*. 58(13):2853-2863 (1994).

Templeton et al., "Variable carbon isotope fractionation expressed by aerobic $CH_4$-oxidizing bacteria," *Geochimica et Cosmochimica Acta* 70:1739-1752, 2006.

Toyama et al., "Construction of insertion and deletion *mxa* mutants of *Methylobacterium extorquens* AM1 by electroporation," *FEMS Microbiology Letters* 166:1-7, 1998.

Vuilleumier et al., "Genome Sequence of the Haloalkaliphilic Methanotrophic Bacterium *Methylomicrobium alcaliphilum* 20Z," *Journal of Bacteriology* 194(2):551-552, Jan. 2012.

Zellner et al., "A study of three anaerobic methanogenic bioreactors reveals that syntrophs are diverse and different from reference organisms," *FEMS Microbiology Ecology* 22:295-301, 1997.

Stein et al., "Genome Sequence of the Obligate Methanotroph *Methylosinus trichosporium* Strain OB3b," *Journal of Bacteriology* 192(24):6497-6498 (Dec. 2010).

Bowman et al., "Phospholipid fatty acid and lipopolysaccharide fatty acid signature lipids in methane-utilizing bacteria," *FEMS Microbiology Ecology* 85:15-22 (1991).

Knothe, "Biodiesel and renewable diesel: A comparison," *Progress in Energy and Combustion Science* 36:364-373 (2010).

Liu et al., "Fatty acid production in genetically modified cyanobacteria," *PNAS* 108(17):6899-6904 (Apr. 26, 2011).

Terekhova et al., "Stearic Acid Methyl Ester: A New Extracellular Metabolite of the Obligate Methylotrophic Bacterium *Methylophilus quaylei*," *Applied Biochemistry and Microbiology* 46(2):166-172, 2010.

Weaver et al., "Whole-Cell and Membrane Lipids of the Methylotrophic Bacterium *Methylosinus trichosporium*," *Journal of Bacteriology* 124(2):602-605 (Nov. 1975).

Jahnke et al., "Evidence for the synthesis of the multi-positional isomers of monounsaturated fatty acid in *Methylococcus capsusatus* by the anaerobic pathway," *FEMS Microbiology Letters* 58:183-188 (1989).

* cited by examiner

BIOREFINERY SYSTEM, METHODS AND COMPOSITIONS THEREOF

BACKGROUND

Technical Field

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. But, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of farm land available is not sufficient to satisfy both global food and fuel needs. Therefore, second generation biofuels are being produced from, for example, cellulose or algae. But, technical difficulties in production, along with the high cost of production, have not made second generation biofuels any more cost-effective or accessible.

Third or next generation biofuels made from alternative feedstocks (i.e., not sugar, corn, algae) are needed. In this regard, methane is one of the most abundant domestic carbon feedstocks and is sourced primarily from natural gas. The recent rise in domestic production of methane (from 48 bft$^3$/day in 2006 to 65 bft$^3$/day in 2012) has driven the cost of natural gas to record lows (from about \$14.00/MMBTU in 2006 to about \$2.50/MMBTU in 2012). Domestic natural gas is primarily produced by hydraulic fracturing ("fracking"), but methane can also be obtained from other sources, such as landfills and sewage. In addition, capturing methane sources will have a significant environmental benefit since methane has a 23× greater greenhouse gas contribution relative to $CO_2$.

But, methane's volatility make transportation and direct usage as a fuel problematic. For this reason, there is a strong incentive to convert the gas to a liquid form to allow for easy transport to the point of use. Two main approaches are currently being pursued: liquefaction leading to liquefied natural gas (LNG) and chemical conversion to convert gas-to-liquid (GTL) (Patel, 2005, 7th World Congress of Chemical Engineering, Glasgow, Scotland, UK). The Fischer-Tropsch (F-T) process is currently the most prevalent approach for converting methane from natural gas to higher-order hydrocarbons (Patel, 2005). Note that the F-T process takes syngas as an input which is produced from natural gas by steam reforming (syngas can also be sourced from coal gasification, by high-temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NREL/TP-510-34929). The massive scale required for an F-T plant (more than \$2B capital cost for a typical plant [Patel, 2005]) also represents a significant limitation due to the large amount of methane feedstock required to supply continuous operation of such a plant. As methane transportation is prohibitively expensive in most cases, such a plant must be co-located with either a large gas source or a pipeline. An additional cost and scaling factor is the economics of gas-scrubbing technologies (Spath and Dayton, 2003), as F-T catalysts are highly sensitive to common contaminants in natural gas that survive the syngas conversion process.

F-T plants have been in operation semi-continuously since 1938. Several companies are currently investigating introduction of new plants given the current availability and price of methane discussed above. However, despite significant research and development over the last 70+ years, the limitations of F-T technology prevent broad adoption of commercial GTL processes. The requirements for ready access to large volumes of clean gas, combined with massive capital investment, currently limit natural gas based F-T plants to successful operation in only a few locations worldwide (Spath and Dayton, 2003). The high minimum processing requirement for a GTL or LNG plant, combined with the high cost of transport, result in smaller methane sources being referred to as 'stranded' gas (for example, natural gas produced at off-shore oil wells, or methane off-gas from landfills). In the current absence of efficient small-scale conversion technologies, such stranded gas sources are typically vented to atmosphere or flared, as methane accumulation presents a significant safety risk.

In view of the limitations associated with the production of first, second and next generation biofuels, there is clearly a need in the art for new methods of efficiently and cost-effectively producing alternative fuels without taxing the environment or competing with food production. The present invention solves this problem by providing efficient and cost-effective methods for producing biofuels and other products using bioengineering.

BRIEF SUMMARY

In one aspect, the present disclosure provides a method for making fuel by refining an oil composition derived from a $C_1$ metabolizing non-photosynthetic microorganism in a refining unit to produce fuel. Additionally, this disclosure provides a method for making fuel by converting biomass from a culture primarily comprising a $C_1$ metabolizing non-photosynthetic microorganism into an oil composition and refining the oil composition into a fuel. In yet another aspect, this disclosure provides a biorefinery that includes a processing unit in which an oil composition is derived from a $C_1$ metabolizing non-photosynthetic microorganism; and a refining unit for refining the oil composition to produce a fuel. In still another aspect, the instant disclosure provides a fuel composition having molecules comprising hydrogen and carbon atoms, wherein the hydrogen and carbon atoms are at least 80% of the weight of the composition and wherein the $\delta^{13}C$ distribution of the composition ranges from about −37‰ to about −10‰.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas*. In further preferred embodiments, the $C_1$ metabolizing bacteria are a methanotroph or a methylotroph. Preferred methanotrophs include *Methylomonas, Methylobacter, Methylococcus, Methylosinus, Methylocystis, Methylomicrobium, Methanomonas*, or a combination thereof.

Exemplary methanotrophs include *Methylomonas* sp. 16a (ATCC PTA 2402), *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum*, or a high growth variants thereof. Preferred methylotrophs include *Methylobacterium extorquens, Methylobacterium radiotolerans, Methylobacterium populi, Methylobacterium chloromethanicum, Methylobacterium nodulans*, or a combination thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or a combination thereof. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

DETAILED DESCRIPTION

Figure 1:
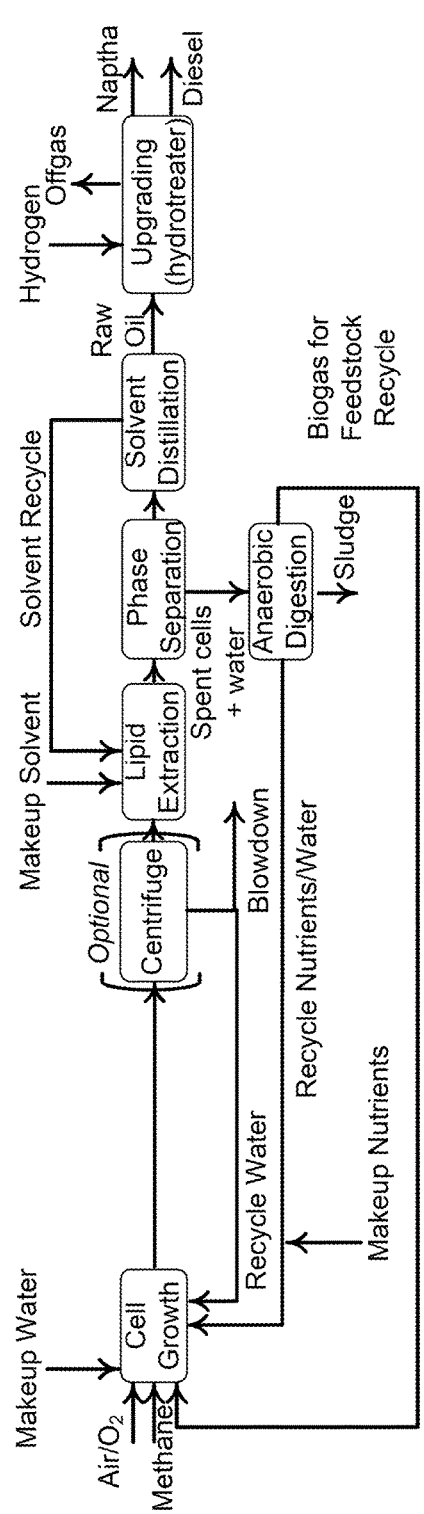
FIG. 1 shows an exemplary conceptual model of a $C_1$ metabolizing microorganism reactor system for methane capture and conversion into an alkane fuel in accordance with certain embodiments of this disclosure.

The instant disclosure provides compositions, methods and systems for generating biofuels and bioplastics, in which $C_1$ metabolizing microorganisms are cultured to generate biomass maximized for bio-oil accumulation. For example, a methane-to-biofuel fermentation process is provided, which is a scalable commercial process. This new approach can use methylotroph or methanotroph bacteria as a new host system to generate biomass for biofuel in the form of, for example, esterified biodiesel or alkane fuels for hydrotreatment, or for bioplastics in form of polyhydroalkanoates (PHAs). Furthermore, an oil composition of interest can be obtained from methylotroph or methanotroph bacteria because these organisms can accumulate significant quantities of membrane lipids under conditions described herein and, moreover, these microorganisms produce high membrane content.

By way of background, methane from a variety of sources, including natural gas, represents an abundant domestic resource. Chemical approaches developing gas-to-liquids (GTL) technology to improve the use of methane as a fuel have met with only limited success to date despite significant investment. In contrast, little effort has been expended to deploy modern bioengineering approaches toward GTL process development. Several limitations, most notably the cost of sugar feedstocks, have prevented the economical production of biofuels using microbial systems. Exploiting inexpensive, domestically abundant carbon feedstocks, such as methane, represents an economically sustainable biofuel production alternative. New production microorganisms have been developed with new bioengineering tools and techniques to provide an industrial-scale GTL bioprocess as described herein. Furthermore, fuel properties following refining and upgrading of extracted lipids demonstrate the drop-in potential for applications such as diesel, gasoline, jet fuel, or olefins.

In one aspect, the present disclosure provides a method for making fuel by refining an oil composition derived from a $C_1$ metabolizing non-photosynthetic microorganism in a refining unit to produce fuel. Additionally, this disclosure provides a method for making fuel by converting biomass from a culture primarily comprising a $C_1$ metabolizing non-photosynthetic microorganism into an oil composition and refining the oil composition into a fuel. In another aspect, this disclosure provides a biorefinery that includes a processing unit in which an oil composition is derived from a $C_1$ metabolizing non-photosynthetic microorganism; and a refining unit for refining the oil composition to produce a fuel.

In still another aspect, the instant disclosure provides a fuel composition having molecules comprising hydrogen and carbon atoms, wherein the hydrogen and carbon atoms are at least 80% of the weight of the composition and wherein the $\delta^{13}C$ distribution of the composition ranges from about −37‰ to about −10‰.

Prior to setting forth this disclosure in more detail, it may be helpful to an understanding thereof to provide definitions of certain terms to be used herein. Additional definitions are set forth throughout this disclosure.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, "$C_1$ substrate" or "$C_1$ compound" refers to any carbon containing molecule or composition that lacks a carbon-carbon bond. Exemplary molecules or compositions include methane, methanol, formaldehyde, formic acid or a salt thereof, carbon monoxide, carbon dioxide, syngas, methylamines (e.g., monomethylamine, dimethylamine, trimethylamine), methylthiols, or methylhalogens.

As used herein, "$C_1$ metabolizing microorganism" or "$C_1$ metabolizing non-photosynthetic microorganism" refers to any microorganism having the ability to use a single carbon ($C_1$ substrate as a source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as Methanotrophs and Methylotrophs) and yeast. In preferred embodiments, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy are $C_1$ substrates and nothing else.

As used herein, the term "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria that have the ability to oxidize methane as it primary source of carbon and energy. Exemplary methanotrophic bacteria include *Methylomonas, Methylobacter, Methylococcus, Methylosinus, Methylocystis, Methylomicrobium*, or *Methanomonas*. In certain other embodiments, the methylotrophic bacterium is an "obligate methylotrophic bacterium," which refers to bacteria that are limited to the use of $C_1$ substrates for the generation of energy.

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, such as coal, coal oil, natural gas, biomass, and waste organic matter. CO utilizing bacterium does not include bacteria that must be genetically modified for growth on CO as its carbon source.

As used herein, "syngas" refers to a mixture of carbon monoxide (CO) and hydrogen ($H_2$). Syngas may also include $CO_2$, methane, and other gases in smaller quantities relative to CO and $H_2$.

"Growth" is defined as an increase in cell mass. This may occur through cell division (replication) and the formation of new cells during "balanced growth," or during "unbalanced growth" when cellular mass increases due to the accumulation of a polymer, such as certain lipids. In the latter case, growth may be manifest as an increase in cell size due to the accumulation of a biopolymer within the cell.

During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polydroxyalkanoates (PHAs), including polyhydroxybutyrate (PHB), polyhdroxyvalerate (PHV), and polyhydroxyhexanoate (PHHx)-glycogen, or secreted materials, such as extracellular polysaccharide. Such oil compositions are useful in the production of bioplastics.

Exemplary balanced and unbalanced growth conditions may differ in the nitrogen content in the media. For example, nitrogen constitutes about 12% of dry cell weight, which means that 12 mg/L nitrogen must be supplied (along with a feedstock and other nutrients in the required stoichiometric ratios) to grow 100 mg/L dry cell weight. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

The term "exponential growth", "exponential phase growth", "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases. The term "growth-altering environment" refers to energy, chemicals, or living things that have the capacity to either inhibit cell growth or kill cells. Inhibitory agents may include mutagens, drugs, antibiotics, UV light, extreme temperature, pH, metabolic byproducts, organic chemicals, inorganic chemicals, bacteria, viruses, or the like.

As used herein, "high growth variant" refers to a organism, microorganism, bacterium, yeast, or cell capable of growth with a $C_1$ substrate, such as methane or methanol, as the sole carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689,601).

As used herein, "biofuel" refers to a fuel at least partially derived from "biomass."

As used herein, "biomass" refers to organic material having a biological origin, which may include whole cells, lysed cells, extracellular material, or the like. For example, the material harvested from a cultured microorganism (e.g., bacterial or yeast culture) is considered the biomass, which can include secreted products. Such a culture may be considered a renewable resource.

As used herein, "oil composition" refers to the lipid content of a biomass, including fatty acids, triglycerides, phospholipids, polyhyroxyakanoates, isoprenes, terpenes, or the like. An oil composition of a biomass may be extracted from the rest of the biomass material by methods described herein, such as by hexane extraction. In addition, an "oil composition" may be found in any one or more areas of a culture, including the cell membrane, cell cytoplasm, inclusion bodies, secreted or excreted in the culture medium, or a combination thereof.

As used herein, "biorefinery" refers to a facility that integrates biomass conversion processes and equipment to produce fuels from biomass.

As used herein, "refinery" refers to an oil refinery, or aspects thereof, at which oil compositions (e.g., biomass, biofuel, or fossil fuels such as crude oil, coal or natural gas) may be processed. Exemplary processes carried out at such refineries include cracking, transesterification, reforming, distilling, hydroprocessing, isomerization, or any combination thereof.

As used herein, "recombinant" or "non-natural" refers to an organism microorganism, cell, nucleic acid molecule, or vector that has at least one genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a cell having one or more such modifications. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all. In another example, genetic modifications to nucleic acid molecules encoding enzymes or functional fragments thereof can provide biochemical reaction(s) or metabolic pathway capabilities to a recombinant microorganism or cell that is new or altered from its naturally occurring state.

As used herein, "heterologous" nucleic acid molecule, construct or sequence refers to a nucleic acid molecule or portion of a nucleic acid molecule sequence that is not native to a cell in which it is expressed or is a nucleic acid molecule with an altered expression as compared to the native expression levels in similar conditions. For example, a heterologous control sequence (e.g., promoter, enhancer) may be used to regulate expression of a gene or a nucleic acid molecule in a way that is different than the gene or a nucleic acid molecule is normally expressed in nature or culture. Generally, heterologous nucleic acid molecules are not endogenous to the cell or part of the genome in which they are present, and have been added to the cell by conjugation, transformation, transfection, electroporation, or the like.

Biofuel Production Systems

The systems for generating biofuels of the instant disclosure may include separate units (e.g., close or adjacent to each other, or not), integrated units, or the system itself may be interconnected and integrated. The systems of this disclosure may use biomass from a microorganism grown in an integrated biorefinery to generate fuel products. In certain embodiments, a biorefinery uses a single biomass or a mixed biomass to generate fuel (e.g., diesel fuel, jet fuel, gasoline), such as a $C_1$ metabolizing microorganism (e.g., a methanotroph such as *Methylosinus trichosporium* OB3b, *Methylococcus capsulatus* Bath, *Methylomonas* sp. 16a, *Methylomicrobium alcaliphilum*, or a high growth variants thereof) as the biomass.

An exemplary biorefinery system is illustrated in FIG. 1. Such a system can perform one or more of the following steps: culturing a microorganism strain of interest (e.g., a methanotroph, methylotroph or yeast) which may have one or more improved properties (e.g., higher growth rate, ability to grow in high pH, improved utilization of nutrients, temperature stability, increased biomass yield), recovering a product such as an oil composition (e.g., fatty acids, triglycerides, phospholipids, isoprenes, terpenes, PHA) from the microorganism, and refining the oil composition to produce plastic prescursors or one or more fuels, such as jet fuel, diesel fuel, gasoline, or a combination thereof. Different fuel products can be produced by the system simultaneously or in series. For example, the system can include a hydrotreating plant or unit that can convert the oil composition to jet fuel and diesel. The system can also include a petroleum refinery that can convert the crude oil and products from the hydrotreating plant to gasoline. For example, the production of jet fuel and diesel fuel can result in additional products, such as naphtha and light hydrocarbons, such as propane, that are then used for generating gasoline. Exemplary light hydrocarbons include methane, ethane, propane, butane, butanol, and isobutanol. In another example, production of gasoline can result in additional products, such as diesel, which can be used for producing jet fuel.

Figure 2:
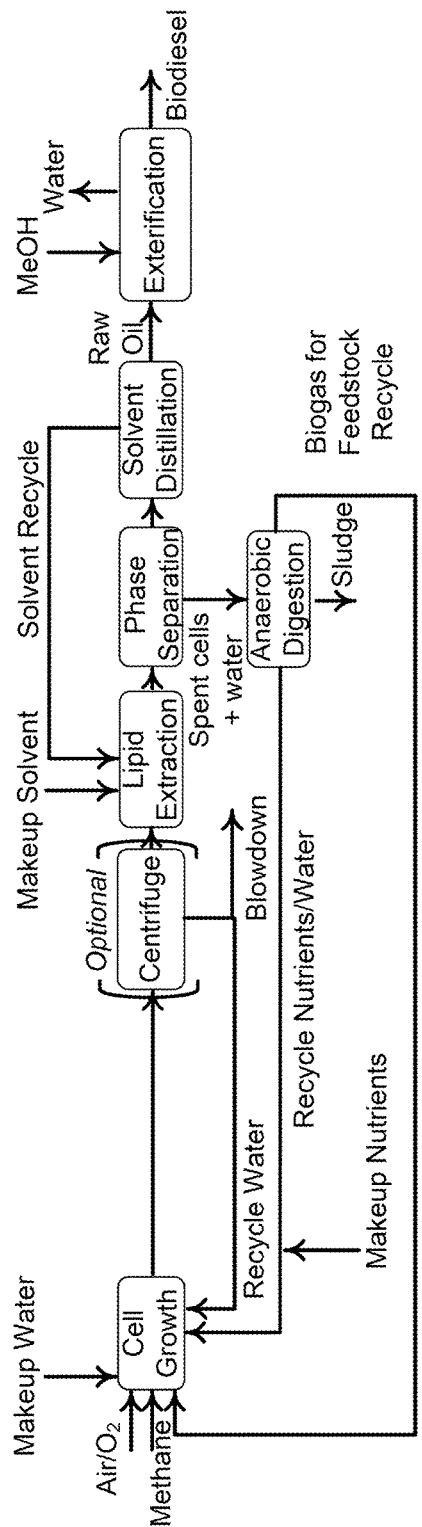
FIG. 2 shows an exemplary conceptual model of a $C_1$ metabolizing microorganism reactor system for methane capture and conversion into biodiesel in accordance with certain embodiments of this disclosure.

An alternative exemplary biorefinery system is illustrated in FIG. 2. Such a system can perform one or more of the following steps: culturing a microorganism strain of interest (e.g., a methanotroph, methylotroph or yeast) which may have one or more improved properties (e.g., higher growth rate, ability to grow in high pH, improved utilization of nutrients, temperature stability, increased biomass yield), recovering a product such as an oil composition (e.g., fatty acids, triglycerides, phospholipids, isoprenes, terpenes, PHA) from the microorganism, and modifying the oil composition to produce a biodiesel composition. For example, the system can include an esterification plant or unit that can convert the oil composition to biodiesel by reaction with an alcohol. Exemplary alcohols include methanol, ethanol, propanol, or longer chain fatty alcohols.

In some embodiments, the systems disclosed herein use bacteria, such as methylotrophs or methanotrophs, or yeast as the microorganism. The bacteria or yeast can be harvested and separated from the culture media (if not grown as, for example, as a biofilm), resulting in a bacterial or yeast paste. The bacterial or yeast biomass may optionally be dried prior to obtaining an oil composition from the biomass. In certain embodiments, the bacterial or yeast biomass remains wet to some extent and need not be fully dried before the oil composition is separated or extracted. Bacterial or yeast oil compositions may be extracted from the biomass and be separated from the bacterial or yeast solids or sludge. Extraction of an oil composition may be accomplished using various different solvents (e.g., a polar solvent, a non-polar solvent, a neutral solvent, an acidic solvent, a basic solvent, hexane, or a combination thereof), such as hexane or acidic methanol or chloroform/methanol mix, in processes such as those described in more detail herein or other extraction methods known in the art.

In certain embodiments, an oil composition of the present disclosure is refined. Refining may include cracking, transesterification, reforming, distilling, hydroprocessing, isomerization, or a combination thereof. Optionally, refining can involve removal of contaminants. For example heteroatoms and metals can be removed by hydrotreating (e.g., hydrodenitrogenation (HDN), hydrodeoxygenation (HDO), hydrodesulfurization (HDS), hydrodemetallization (HDM)). Hydrotreatment may also be saturation of olefins, distillate hydrotreating, vacuum gas oil hydrotreating, fixed-bed residue hydrotreating, or a combination thereof. Hydrotreatment of an oil composition can produce jet fuel or diesel. The oil composition can also be refined by cracking, such as catalytic cracking to produce gasoline. Representative cracking processes may include catalytic cracking, fluid catalytic cracking, steam cracking, hydrocracking, thermal cracking, thermal catalytic cracking, or a combination thereof. The refining by hydrotreating and cracking can occur concurrently (both processes occurring) or alternatively (one or the other is occurring). The refining processes can also be subsequent to each other, for example, products produced by hydrotreatment, can then be processed by cracking Products from one refining process (e.g., $H_2$) can also be further used by another refining process. The refining processes can be separate units of the system, or in the same unit. Moreover, the bacterial or yeast solids or sludge can be used to produce fuels, animal feed, or energy, such as methane released from digestion of the solids or sludge.

In certain embodiments, the instant disclosure provides a biorefinery comprising (a) a processing unit in which an oil composition is derived from a $C_1$ metabolizing non-photosynthetic microorganism; and (b) a refining unit for refining the oil composition to produce a fuel. In further embodiments, the biorefinery may further comprise a controlled culturing unit for culturing a $C_1$ metabolizing non-photosynthetic microorganism in the presence of a feedstock comprising a $C_1$ substrate, wherein the cultured bacteria produce the oil composition.

Exemplary controlled culturing units include a fermentor, a bioreactor, a hollow fiber cell, or the like. In further embodiments, the culture may be grown in the form of a liquid-phase fermentation or a solid phase fermentation. For example, bacteria such as methylotrophs or methanotrophs may be cultured in a balanced media, or cultured in an unbalanced media that has limiting quantities of phosphorus, nitrogen, trace elements, oxygen, or any combination thereof, so that certain lipids or other polymers of interest (e.g., PHAs) accumulate in the cells.

Preferably, embodiments of cultures include a bacterial community, including a variety of methylotrophs or methanotrophs that produce the highest levels of an oil composition of interest (i.e., high w/w ratios of lipids to biomass). A range of bioreactor configurations may be used, including sequencing membrane bioreactors and a continuous multi-stage dispersed growth configuration. In certain embodiments, a bioreactor is operated to select for bacteria that efficiently produce an oil composition of interest from methane, e.g., bioreactor conditions may select against bacteria that either do not produce an oil composition of interest from methane or produce such a composition inefficiently.

In further embodiments, the present disclosure provides a controlled culturing unit in which a $C_1$ substrate (e.g., methane) is delivered in a gas phase to microbial biofilms in a solid phase fermentation. In other embodiments, balanced or unbalanced growth conditions are established in a solid phase fermentation. In still other embodiments, methylotrophs or methanotrophs are grown under balanced growth conditions, harvested and separated from liquid phase, and transferred to a solid phase fermentation chamber where $C_1$ substrate is delivered under unbalanced conditions (e.g., nitrogen is not included) and the bacteria consume the substrate to generate an oil composition of interest.

In certain embodiments, the instant disclosure provides a biorefinery comprising (a) a controlled culturing unit for culturing a $C_1$ metabolizing non-photosynthetic microorganism in the presence of a feedstock comprising a $C_1$ substrate, wherein the cultured bacteria produce the oil composition; (b) a processing unit in which an oil composition is derived or extracted from a $C_1$ metabolizing non-photosynthetic microorganism; and (c) a refining unit for refining the oil composition to produce a fuel. In further embodiments, the feedstock $C_1$ substrate used in the biorefinery is methane, methanol, formaldehyde, formic acid or a salt thereof, carbon monoxide, carbon dioxide, syngas, a methylamine, a methylthiol, or a methylhalogen.

In a preferred biorefinery embodiment, the $C_1$ metabolizing non-photosynthetic microorganism is a methanotroph or methylotroph, the feedstock $C_1$ substrate is methane, and the bacteria are cultured under aerobic conditions. The methanotroph can be *Methylosinus trichosporium* OB3b, *Methylococcus capsulatus* Bath, *Methylomonas* sp. 16a, *Methylomicrobium alcaliphilum*, a combination thereof, or a high growth variant thereof, and the methylotroph can be *Methylobacterium extorquens, Methylobacterium radiotolerans, Methylobacterium populi, Methylobacterium chloromethanicum, Methylobacterium nodulans*, a combination thereof, or a high growth variant thereof. In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

In certain embodiments, the biorefinery processing unit is capable of deriving the oil composition by a wet extraction, a supercritical fluid extraction, or a dry extraction. In further embodiments, the wet extraction comprises use of a polar solvent, a non-polar solvent, a neutral solvent, an acidic solvent, a basic solvent, hexane, or a combination thereof. In certain embodiments, the oil composition is derived or extracted from a cell membrane of the $C_1$ metabolizing non-photosynthetic microorganism or may be recovered from a culture supernatant if secreted or excreted or a combination thereof. In further embodiments, the biorefinery further comprises a second processing unit, wherein the second processing unit is a waste processing unit for processing residual matter from the refined oil composition, which includes an anaerobic digester, an aerobic digester, or both. In still further embodiments, the biorefinery further comprises a conduit for delivering at least one product from the waste processing unit for use in culturing or maintaining the $C_1$ metabolizing non-photosynthetic microorganism.

In still further embodiments, the biorefinery processing unit further comprises a controlled culturing unit, wherein the controlled culturing unit is a solid phase fermentation unit in which the culturing and processing (e.g., extraction) can occur in the same unit or even the same chamber. In certain embodiments, the biorefinery combined culturing/processing unit includes supercritical fluid extraction, such as by supercritical fluid comprising $CO_2$.

In certain aspects, any of the aforementioned biorefineries are integrated.

$C_1$ Metabolizing Microorganisms

The $C_1$ metabolizing microorganisms of the instant disclosure may be natural, strain adapted (e.g., performing fermentation to select for strains with improved growth rates and increased total biomass yield compared to the parent strain), or recombinantly modified to produce lipids of interest or to have increased growth rates or both (e.g., genetically altered to express a fatty acid producing enzyme, a formaldehyde assimilation enzyme, or a combination thereof). In certain preferred embodiments, the $C_1$ metabolizing microorganisms are not $C_1$ metabolizing non-photosynthetic microorganisms, such as algae or plants.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*. In further preferred embodiments, the $C_1$ metabolizing bacteria are a methanotroph or a methylotroph. Preferred methanotrophs include *Methylomonas, Methylobacter, Methylococcus, Methylosinus, Methylocystis, Methylomicrobium, Methanomonas*, or a combination thereof. Exemplary methanotrophs include *Methylomonas* sp. 16a (ATCC PTA 2402), *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11, 200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum*, or a high growth variants thereof. Preferred methylotrophs include *Methylobacterium extorquens, Methylobacterium radiotolerans, Methylobacterium populi, Methylobacterium chloromethanicum, Methylobacterium nodulans*, or a combination thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or a combination thereof. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

Each of the microorganisms of this disclosure may be grown as an isolated culture, with a heterologous organism that may aid with growth, or one or more of these bacteria may be combined to generate a mixed culture. In still further embodiments, $C_1$ metabolizing non-photosynthetic microorganisms of this disclosure are obligate $C_1$ metabolizing non-photosynthetic microorganisms.

Culture Methods and Methods of Making Oil Compositions

A variety of culture methodologies may be used for the microorganism, bacteria and yeast described herein. For example, $C_1$ metabolizing microorganisms (such as methanotroph or methylotroph bacteria) may be grown by batch culture and continuous culture methodologies. In certain embodiments, the cultures are grown in a controlled culture unit, such as a fermentor, bioreactor, hollow fiber cell, or the like. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then are allowed to grow without adding anything to the system. As used herein, a "batch" culture is in reference to not changing the amount of a particular carbon source initially added, whereas control of factors such as pH and oxygen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measureable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, 1992, Appl. Biochem. Biotechnol. 36:227).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, by-products, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some *Candida* species can metabolize alanine or oleic acid (Sulter et al., Arch. Microbiol. 153:485-489, 1990). *Methylobacterium extorquens* AM1 is capable of growth on a limited number of $C_2$, $C_3$, and $C_4$ substrates (Van Dien et al., Microbiol. 149:601-609, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In further embodiments, the oil composition is derived or extracted from cell membrane of the $C_1$ metabolizing non-photosynthetic microorganism (e.g., methylotroph, methanotroph, yeast) or may be recovered from a culture supernatant if secreted or excreted, or a combination thereof.

In certain embodiments, the instant disclosure provides a method for making fuel by refining an oil composition in a refining unit to produce fuel, wherein the oil composition is derived from a $C_1$ metabolizing non-photosynthetic microorganism, such as a methylotroph or methanotroph. In further embodiments, the method further comprises use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produce an oil composition; (b) extracting the oil composition from the cultured bacteria in a processing unit; and (c) refining the extracted oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

Fuel Compositions

By way of background, stable isotopic measurements and mass balance approaches are widely used to evaluate global sources and sinks of methane (see Whiticar and Faber, *Org. Geochem.* 10:759, 1986; Whiticar, *Org. Geochem.* 16: 531, 1990). To use $\delta^{13}C$ values of residual methane to determine the amount oxidized, it is necessary to know the degree of isotopic fractionation caused by microbial oxidation of methane. For example, aerobic methanotrophs metabolize methane through a specific enzyme, methane monooxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or Serine cycles (Hanson and Hanson, *Microbiol. Rev.* 60:439, 1996), which are directly analogous to carbon assimilation pathways in photosynthetic organisms. More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in Templeton et al. (*Geochim. Cosmochim. Acta* 70:1739, 2006), which methods are hereby incorporated by reference.

A fuel product as described herein may be a product generated by blending a composition and a fuel component. In some instances, the fuel product has a $\delta^{13}C$ distribution of greater than −37‰. In other instances, the fuel product has a $\delta^{13}C$ distribution of less than =32‰. For example, a composition extracted from an organism can be blended with a fuel component prior to refining (for example, cracking) in order to generate a fuel product as described herein. The composition can be an oil composition extracted from the organism that comprises a composition wherein the hydrogen and carbon atoms are at least 80% of the weight of the composition, and wherein the $\delta^{13}C$ distribution of the composition is less than −37‰. A fuel component, as described, can be a fossil fuel, or a mixing blend for generating a fuel product. For example, a mixture for fuel blending may be a hydrocarbon mixture that is suitable for blending with another hydrocarbon mixture to generate a fuel product. For example, a mixture of light alkanes may not have a certain octane number to be suitable for a type of fuel, however, it can be blended with a high octane mixture to generate a fuel product.

In certain embodiments, a fuel composition comprises molecules having hydrogen and carbon atoms, wherein the hydrogen and carbon atoms are at least 80% of the weight of the composition and wherein the $\delta^{13}C$ distribution of the composition ranges from about −37‰ to about −10‰, or wherein the $\delta^{13}C$ distribution in the biomass increases as cell density increases from −22‰ to −9‰, or wherein the $\delta^{13}C$ composition of the biomass was higher than $CO_2$ produced at the same time by an average of 5% to 15% when cultured in the presence or absence of copper. In further embodiments, wherein the hydrogen and carbon atoms are at least 85%, 90%, 95%, 99%, or 100% of the weight of the composition. In still other embodiments, the composition is a liquid, or is a fuel additive or a fuel product. In certain embodiments, the composition is a terpene, terpenoid, isoprene, or an isopreniod. In still other embodiment, the composition has an octane number of 85-120 or an octane number greater than 90.

EXAMPLES

Example 1

Exemplary Biofuel Production

Culture Maintenance

*Methylosinus trichosporium* OB3b was maintained at 30° C. in serum vials containing Higgins minimal nitrate salts medium (NSM). The headspace composition was adjusted to a 50:50 volume of methane:air. The vials were shaken at a rate of 200-250 rpm. Alternatively, the culture was maintained on NSM-media plates solidified with 1.5% w/v agar grown in the presence of methanol vapor (via 0.5 mL methanol in the lid of parafilm-sealed plates) or supplemented with 1% methanol. Plates were incubated inverted in a humidified chamber under normal atmosphere at 30° C.

Methanotroph Fermentation

A 2-liter bioreactor containing 1 L defined media MM-W1 was inoculated with cells from serum vial batch culture (10-20% v/v). The composition of medium MM-W1 was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 1 μM $CuSO_4*5H_2O$, 10 μM FeEDTA, and 1 mL trace metal solution (containing, per L: 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and FeEDTA were added after media was autoclaved and cooled. The reactor contents were stirred with an overhead impeller at a constant 800 rpm. The culture was fed with a constant methane sparging at 75 mL/min, while pure oxygen was supplied at a variable rate of 30-100 mL/min to maintain a dissolved oxygen level of 60-90% (relative to air saturation of the media). Temperature in the bioreactor was maintained at 30° C. and pH was maintained at 7.1±0.1 using automated addition of 0.5 M NaOH and 1 M HCl. Additions were made to the culture every 4-24 hours (corresponding to an $OD_{600}$ increase of approximately 5 OD units). The additions alternated between a metal addition (10 μM $CuSO_4$, 5 μM $FeSO_4$, 5 μM $Fe^{III}$-EDTA final concentration) and a nutrient addition (5.75 mM $K_xH_yPO_4$, 10 mM $NaNO_3$). Under these conditions, essentially linear growth is observed, with effective biomass generation rate 2.7 to 3.3 grams dry cell weight per liter per day to an $OD_{600}$ of greater than 20.

Semi-Continuous Fermentation:

Harvesting of the accumulated biomass is performed at approximately 12-24 hour intervals, as the culture density approaches (but did not enter) stationary phase. Approximately half of the bioreactor volume is removed by transferring to a separate container via centrifugal pump. An equal volume of fresh or recycled media is then returned to the bioreactor such that the optical density of the reactor is approximately half of its initial value. The culture fermentation is continued according to the above protocol. The harvested biomass is optionally concentrated by centrifugation or filtration and then subjected to an extraction process.

Extraction

A methanotroph oil composition contained within the harvested biomass is separated from biomass using high-shear contact with hexane and a conditioning agent. The oil dissolves into hexane, or other similar solvents, forming a solution of miscella. Water and cellular solids do not dissolve, and is collected separately from the miscella. The immiscibility of water and hexane is used to produce the desired separation. Following high-shear mixing, the methanotroph/hexane/water mixture is sent to a decanter where it separates into two distinct liquids: a lighter hexane and oil phase (miscella), and a heavier water and spent solids phase.

Miscella from the decanter is fed to a distillation process where the methanotroph oil composition is separated from the solvent. This allows recovery and reuse of the solvent, and purifies the oil to a point where it is ready for downstream processing. Distillation takes advantage of the difference in boiling points of the solvent and oil to separate the two components.

Optionally, solids in the water phase are concentrated using a centrifuge or other mechanical concentration equipment. The water removed from the solids may be recycled, while the solids, with some residual water, can be fed to a solids processing unit.

Refining

The extracted oil composition is transported to a refinery. The refinery converts triglycerides from bio-renewable feeds such as fats, greases, and methanotroph oils into a mixture of liquid hydrocarbon fuels, primarily biodiesel and biojet fuel, a high quality synthetic paraffinic kerosene (SPK). The refinery can be run in two different modes: a Mixed Mode, wherein output is a mixture of biodiesel and biojet fuel, and a Diesel Mode, wherein output is primarily biodiesel.

During refining, the fatty acids and glycerides are converted to SPK in three steps. First, raw feedstocks are treated to remove catalyst contaminants and water. In the second step, fatty acid chains are transformed into n-paraffins in a hydrotreater. The example of oleic acid conversion to n-octadecane via the hydrogenation and deoxygenation reactions in the hydrotreater.

For most bio-oils, fats, and greases, the hydrotreater liquid product is mainly a $C_{15}$-$C_{18}$ n-paraffin composition. In the third step of the process, these long straight-chain paraffins are hydrocracked into shorter branched paraffins. The hydrocracked products fall mainly in the kerosene boiling range.

SPK meets or exceeds all jet fuel fit-for-purpose specifications except density. The high hydrogen-to-carbon ratio of SPK, which gives its excellent thermal stability and low participate emission attributes, means a lower density hydrocarbon composition: 760-770 kg/m$^3$ compared to the minimum ASTM specification value of 775 kg/m$^3$. However, this is not an issue with 50/50 blends of petroleum jet fuel and SPK.

The process requires hydrogen, which can be produced on-site using methane reforming, or can be provided by co-locating the facility at an existing refinery.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. patent application Ser. No. 13/940,861 and U.S. Provisional Patent Application No. 61/671,542, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for making fuel, comprising converting biomass from a culture primarily comprising methanotrophic bacteria grown under unbalanced growth conditions on a $C_1$ substrate comprising methane and/or methanol as a carbon source, into an oil composition and refining the oil composition into a liquid fuel, wherein the methanotrophic bacteria grown under unbalanced growth conditions contain an increased amount of lipid to total biomass yield as compared to a parent methanotrophic bacteria grown under balanced growth conditions, and wherein the culture is a mixed culture comprising the methanotrophic bacteria and one or more heterologous organisms.

2. The method of claim 1, wherein the oil composition is from cell membrane of the methanotrophic bacteria.

3. The method of claim 1, wherein the $C_1$ substrate is natural gas or methane.

4. The method of claim 1, wherein the culture is grown in a controlled culturing unit, the controlled culturing unit being a fermentor or bioreactor.

5. The method of claim 1, wherein the culture is from a liquid-phase fermentation or a solid phase fermentation.

6. The method of claim 1, wherein the biomass is converted into an oil composition by extraction, wherein the extraction is selected from a wet extraction, a supercritical fluid extraction, or a dry extraction.

7. The method of claim 6, wherein the extraction is a wet extraction, which comprises use of a polar solvent, nonpolar solvent, neutral solvent, acidic solvent, hexane, or any combination thereof.

8. The method of claim 4, wherein the controlled culturing unit is a solid phase fermentation unit and the oil composition is extracted from the biomass by supercritical fluid extraction.

9. The method of claim 8, wherein the supercritical fluid comprises $CO_2$.

10. The method of claim 1, wherein the oil composition is refined by a process of cracking, transesterification, reforming, distilling, hydroprocessing, isomerization, or a combination thereof.

11. The method of claim 10, wherein the hydroprocessing is hydrogenation, hydrotreating, hydrocracking, hydroisomerization, or a combination thereof.

12. The method of claim 11, wherein the hydrotreating is hydrodenitrogenation (HDN), hydrodeoxygenation (HDO), hydrodesulfurization (HDS), hydrodemetallization (HDM), saturation of olefins, distillate hydrotreating, vacuum gas oil hydrotreating, fixed-bed residue hydrotreating, or a combination thereof.

13. The method of claim 10, wherein the cracking is catalytic cracking, fluid catalytic cracking, steam cracking, hydrocracking, thermal cracking, thermal catalytic cracking, or a combination thereof.

14. The method of claim 1, wherein the liquid fuel comprises jet fuel, diesel fuel, paraffinic kerosene, gasoline, or any combination thereof.

15. The method of claim 1, wherein the methanotrophic bacteria is a *Methylomonas, Methylobacter, Methylococcus, Methylosinus, Methylocystis, Methylomicrobium, Methanomonas*, or a combination thereof.

16. The method of claim 1, wherein the methanotrophic bacteria is a *Methylomonas* sp. 16a, *Methylosinus trichosporium, Methylosinus sporium, Methylocystis parvus, Methylomonas methanica, Methylomonas albus, Methylobacter capsulatus, Methylobacterium organophilum, Methylomonas* sp. AJ-3670, *Methylocella silvestris, Methylacidiphilum infernorum, Methylibium petroleiphilum, Methylomicrobium alcaliphilum*, or a high growth variant thereof.

17. The method of claim 1, wherein the methanotrophic bacteria is *Methylobacterium extorquens, Methylobacterium radiotolerans, Methylobacterium populi, Methylobacterium chloromethanicum, Methylobacterium nodulans*, or a high growth variant thereof.

18. The method of claim 1, wherein the methanotrophic bacteria is an obligate methanotrophic bacteria.

19. The method of claim 1, wherein the methanotrophic bacteria is a recombinant methanotrophic bacteria comprising a heterologous polynucleotide encoding a fatty acid producing enzyme, a formaldehyde assimilation enzyme, or a combination thereof.

20. The method of claim 1, wherein the biomass is from (a) the methanotrophic bacteria cultured under aerobic conditions with the $C_1$ substrate comprising methane; or (b) methanotrophic bacteria cultured with the $C_1$ substrate comprising methane, and the unbalanced growth condition comprises a limiting nutrient selected from phosphorus, nitrogen, trace elements, oxygen, or any combination thereof.

21. The method of claim 1, wherein the process is carried out at a biorefinery.

22. The method of claim 1, wherein the unbalanced growth conditions comprises methanotrophic bacteria grown on unbalanced media comprising a limiting quantity of phosphorus, nitrogen, trace elements, oxygen, or any combination thereof.

* * * * *